United States Patent
Kobayashi et al.

(10) Patent No.: US 6,420,372 B1
(45) Date of Patent: Jul. 16, 2002

(54) FEBRIFUGINE, ISOFEBRIFUGINE AND METHOD FOR PRODUCING THE SAME

(75) Inventors: Shu Kobayashi, Tokyo; Yusuke Wataya; Hye-Sook Kim, both of Okayama, all of (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/674,362

(22) PCT Filed: Mar. 1, 2000

(86) PCT No.: PCT/JP00/01192

§ 371 (c)(1),
(2), (4) Date: Dec. 22, 2000

(87) PCT Pub. No.: WO00/52005

PCT Pub. Date: Sep. 8, 2000

(30) Foreign Application Priority Data

Mar. 1, 1999 (JP) .............................. 11-052631

(51) Int. Cl.$^7$ ..................... A01N 43/54; A61K 31/505; C07D 239/72
(52) U.S. Cl. ....................... 514/259; 544/287
(58) Field of Search ........................ 514/259; 544/287

(56) References Cited

PUBLICATIONS

Barringer et. al., "The Stereochemistry of Febrifugine . . . ", J. Org. Chem., 1973, vol. 38, No. 10, pp. 1937–1940.*
Burgess et. al., "The Preparation of . . . Piperidines and Pyrrolidines: The Total Synthesis of Febrifugine.", 1996, vol. 37, No. 19, pp. 3255–3258.*
Uesato et al., "Confromational Analysis of Febrifugines . . . ", Chem. Pharm. Bull, 1998, vol. 46(1), pp. 1–5.*
Takeuchi, Y., et al. "Total Synthesis of dl–Febrifugine and dl–Isofebrifugine", Chem. Pharm. Bull., vol. 47, No. 6 (1999), pp. 905–906.
Takeuchi, Y., et al. "Synthesis of D/L–Febrifugine and D/L–Isofebrifugine", Synthesis, No. 10 (1999), pp. 1814–1818.
Takaya, Y., et al. "New type of Febrifugine Analogues, Bearing a Quinolizidine Moiety, Show Potent Antimalarial Activity against Plasmodium Malaria Parasite", J. Med. Chem., vol. 42 (1999), pp. 3163–3166.
Murata, K., et al. "Enhancement of NO Production in Activated Macrophages in Vivo by an Antimalaraial Crude Drug, *Dichroa febrifuga*", J. Nat. Prod., vol. 61 (1998), pp. 729–733.

Uesato, S., et al. "Conformational Analysis of Febrifugines and Halofugines in Organic Solvents", Chem, Pharm. Bull., vol. 46, No. 1 (1998), pp. 1–5.
Barringer, D.F., et al. "The Stereochemistry of Febrifugine. II. Evidence for the Trans Configuration in the Piperidine Ring", J. Org. Chem., vol. 38, No. 10 (1975), pp. 1937–1940.
Burgess, L.E., et al. "The Preparation of =–Substituted, β–Hydroxy Piperidines and pyrrolidines: The Total Synthesis of Febrifugine.", Tetrahedron Letters, vol. 37, No. 19 (1996), pp. 3255–3258.
Kobayashi, S., et al. "Catalytic Asymmetric Synthesis of Antimalarial Alkaloids Febrifugine and Isofebrifugine and Their Biological Activity", J. Org. Chem., vol. 64 (1999), pp. 6833–6841.
Kobayashi, S., et al. "Catalytic Asymmetric Synthesis of Febrifugine and Isofebrifugine", Tetrahedrom Letters, vol. 40 (1999), pp. 2175–2178.

* cited by examiner

Primary Examiner—Mukund J. Shah
Assistant Examiner—Tamthom N. Truong
(74) Attorney, Agent, or Firm—Wenderoth, Lind & Ponack, L.L.P.

(57) ABSTRACT

A febrifugine represented by Formula (A):

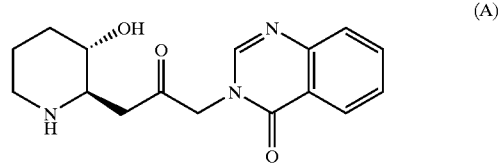

and an isofebrifugine represented by Formula (B):

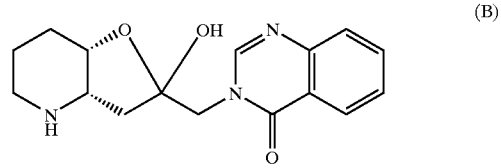

which exhibit extremely strong activities against tropical malarial protozoan are provided, together with a total synthesis route which enables efficient large scale synthesis of the same.

6 Claims, No Drawings

FEBRIFUGINE, ISOFEBRIFUGINE AND METHOD FOR PRODUCING THE SAME

This application is a 371 application of PCT/JP00/01192, filed Mar. 1, 2000.

TECHNICAL FIELD

The present invention relates to febrifugine, isofebrifugine, and a method for producing the same.

BACKGROUND ART

Febrifugine and isofebrifugine derived from Chinese hydrangea are known to have strong activities against tropical malarial protozoan.

The chemical structures of febrifugine and isofebrifugine, known to show such strong activities against malarial protozoan, were reported to be represented by Formulas ($A_0$) and ($B_0$):

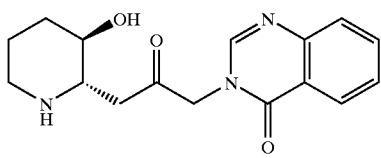

Febrifugine ($A_0$)

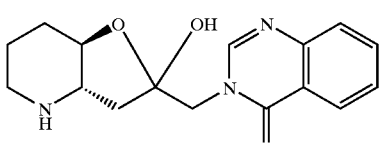

Isofebrifugine ($B_0$)

Although the activity of these febrifugine compounds have been known from old times as active ingredients of Chinese medicines such as "JOSAN", practical isolation and utilization of these compounds have been difficult due to their rarity in nature, and efforts to develop an efficient method for synthesizing them under gentle conditions have not been successful.

Therefore, extensive investigations have been desired, from the viewpoint of efficient synthesis of febrifugines, including the synthesis of analogues, and the view point of the stereochemistry which enables the exertion of bioactivity.

Thus, the objective of the present invention is to thoroughly reinvestigate the basis of such strong activity against malarial protozoan in relation with its stereochemistry, to identify actual substances which exhibit extremely strong activity against tropical malarial protozoan, and to establish a total synthetic route which allows efficient large scale synthesis, by overcoming such conventional circumstances.

DISCLOSURE OF INVENTION

In order to accomplish the above objectives, the present invention provides, firstly, a febrifugine represented by Formula (A):

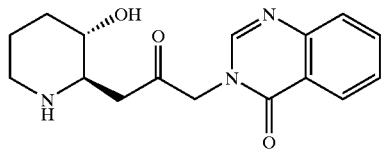

(A)

Secondly, provided by the present invention is an isofebrifugine represented by Formula (B):

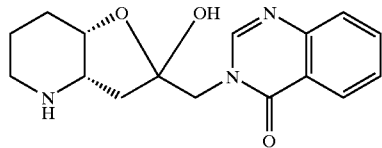

(B)

Thirdly, a febrifugine or an isofebrifugine according to the first or second invention, having an anti-malarial activity is also provided.

Further, as the forth invention, an anti-malarial agent containing, as an active ingredient, a febrifugine or an isofebrifugine according to the first or second invention is also provided.

Furthermore, the present invention provides the following production methods. That is, as the fifth invention, a method for producing febrifugine wherein an S-aldehyde compound represented by Formula (C):

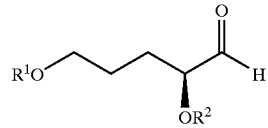

(C)

(wherein $R^1$ represents a silyl group and $R^2$ represents a hydrocarbon group) is subjected to a Mannich reaction with a 2-alkoxyaniline compound and a 2-alkoxypropane compound in the presence of an aqueous Lewis acid of a rare earth metal, in an aqueous solvent, to form a diastereomeric mixture of a β-aminoketone compound represented by Formula (D):

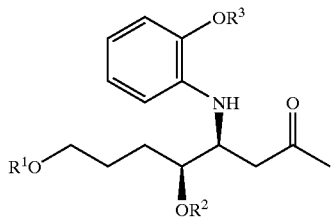

(D)

(wherein $R^1$ and $R^2$ are defined as described above, and $R^3$ represents a hydrocarbon group which forms an alkoxy group of the 2-alkoxyaniline described above), after which the anti-diastereomer is cyclized to form a pyperidine compound, and reacted with a quinazoline compound to obtain a febrifugine represented by Formula (A):

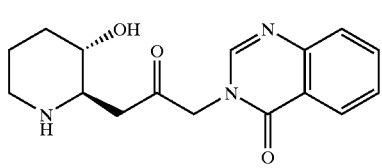

(A)

As the sixth invention, a method for producing isofebrifugine wherein an S-aldehyde compound represented by Formula (C):

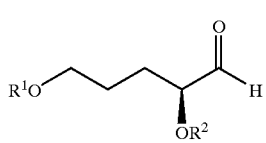

(C)

(wherein $R^1$ represents a silyl group and $R^2$ represents a hydrocarbon group) is subjected to a Mannich reaction with a 2-alkoxyaniline compound and a 2-alkoxypropane compound in the presence of an aqueous Lewis acid of a rare earth metal, in an aqueous solvent, to form a diastereomeric mixture of a β-aminoketone compound represented by Formula (D):

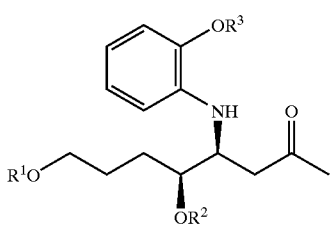

(D)

(wherein $R^1$ and $R^2$ are defined as described above, and $R^3$ represents a hydrocarbon group which forms an alkoxy group of the 2-alkoxyaniline described above), after which the syn-diastereomer is cyclized to form a pyperidine compound, and reacted with a quinazoline compound to obtain a isofebrifugine represented by Formula (B):

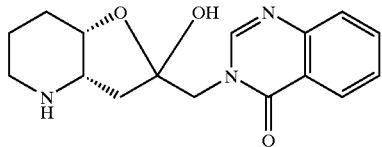

(B)

is also provided.

Provided as the seventh invention is a method for producing a febrifugine or an isofebrifugine according to the fifth or sixth invention, wherein a silyloxypropanal represented by Formula (E):

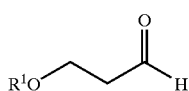

(E)

(wherein $R^1$ represents a silyl group) and an ethene compound represented by Formula (F):

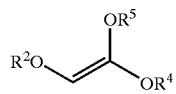

(F)

(wherein $R^2$ and $R^4$ each represents a hydrocarbon group and $R^5$ represents a silyl group) are subjected to an asymmetric aldol condensation in the presence of a chiral tin (II) Lewis acid catalyst, to form an addition reaction product represented by Formula (G):

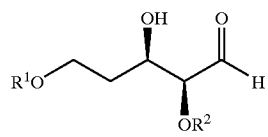

(G)

(wherein $R^1$, $R^2$ and $R^4$ are defined as described above), dehydroxylated, and reduced to form an aldehyde compound of Formula (C), which is then subjected to a Mannich reaction.

Furthermore, as the eighth invention, a method for producing febrifugine or isofebrifugine according to the fifth or sixth invention, wherein an aldehyde compound represented by Formula (C) is reacted with a 2-alkoxydianiline compound and a 2-alkoxypropene compound by a Mannich reaction in water, in the presence of a Lewis acid-surfactant-integrated catalyst to form a β-aciketone compound, is provided.

As described above, the present invention provides, by investigating extensively the product obtained through the established novel production method, novel substances represented by the above Formulas (A) and (B), as febrifugine and isofebrifugine expressing strong activity against tropical malarial protozoan.

Moreover, the present invention provides a production method which enables convenient and efficient large scale production of such novel substances.

BEST MODE FOR CARRYING OUT THE INVENTION

While the aspects of the invention are as stated above, the embodiments of the invention are as described below.

First, a febrifugine and an isofebrifugine according to the invention may be specified as (2'R, 3'S)-febrifugine represented by Formula (A) and (2'S, 3'S)-isofebrifugine represented by Formula (B), respectively, and are distinct in terms of their absolute configuration, from conventional (2'S, 3'R)- and (2'R, 3'R)-compounds represented by the above Formulas ($A_0$) and ($B_0$).

Next, in the production of such compounds according to the present invention, an S-aldehyde compound represented by the above Formula (C), is the first key intermediate in the synthetic route. The second key intermediate is a β-aminoketone compound represented by the above Formula (D).

The symbol R' in Formulas (C), (D), (E), (F) and (G) represents a silyl group which may be a hydrocarbon group, same or different, bonded to an Si atom. Examples of a trialkylsilyl group may be t-butyldimethylsilyl, trimethylsilyl groups and so on. $R^2$ may be any one of various hydrocarbon groups which form protective groups. An example would be a benzyl group. $R^3$ may also be any hydrocarbon group, such as an alkyl group including methyl, ethyl, and so on. $R^4$ is also a hydrocarbon. An example would be a phenyl group. $R^5$ is a silyl group, which may vary as described for R'.

An aldol addition product (G) from which an aldehyde compound (C) is derived, is produced by an asymmetric aldol reaction, in which a chiral metal compound obtained from a metal compound and a chiral amine compound may be employed as a catalyst. For example, a chiral metal compound catalyst obtained from a triflate or perchlorate such as tin (II), and a chiral amine compound is useful.

The reaction may also be performed in an organic solvents such as ethers and nitrites.

One which is especially useful is a chiral tin (II) catalyst.

Also, the Mannich reaction by which compound (D) is derived from the above compound (C), may be performed in the presence of an aqueous Lewis acid catalyst of a rare earth metal.

For example, a triflate or a perchlorate of a rare earth metal such as ytterbium (Yb) and scandium (Sc) may be used.

Furthermore, a Lewis acid-surfactant-integrated catalyst may be employed in the Mannich reaction described above. Such catalyst may be any of the various salts of transition metals with surfactant compounds, such as scandium dodecylsulfate (STDS) obtained by mixing scandium chloride and sodium dodecylsulfate in water, as well as sulfonate compounds. The reaction may be performed in water, and the procedures are very simple.

The embodiments of the present invention are further described in reference to the following Examples. These Examples are not intended to restrict the invention in any sense. It is also a matter of course that a reaction method known per se may be employed in any relevant step.

EXAMPLES

Example 1

Production of Aldehyde Compound (C)

An aldehyde compound (C) was prepared according to the reaction scheme shown below.

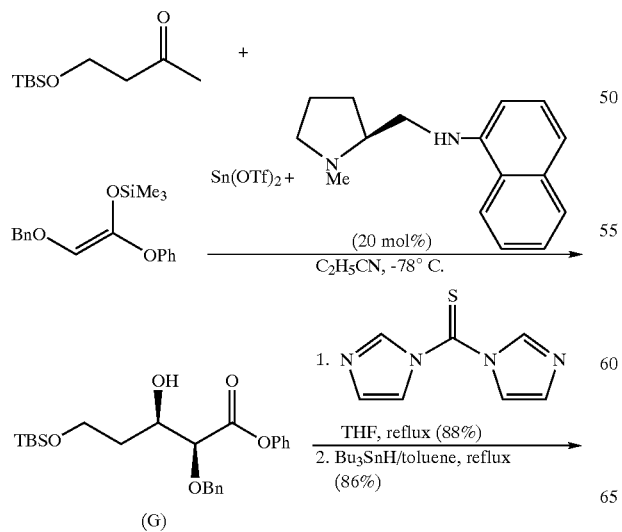

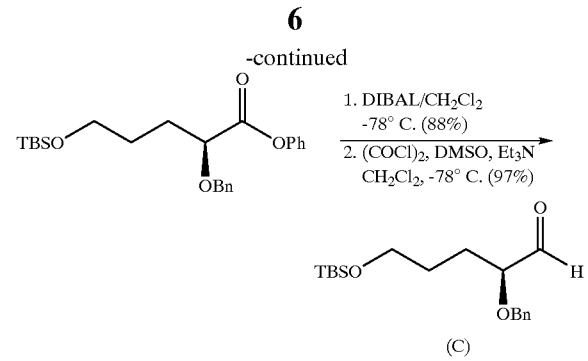

That is, in the presence of a chiral tin (II) Lewis acid (20 mol %) obtained from tin (II) triflate and a chiral diamine compound, 3-t-butyldimethylsilyloxypropanal was reacted with 2-benzyloxy-1-trimethylsilyloxy-1-phenoxyethene in a solvent of propionitrile, at −78° C., to obtain the corresponding aldol-type addition reaction product, at 70% yield, with an excellent diastereo- and enantio-selectivity.

The product thus obtained was dehydroxylated at the 3-position in two steps, as indicated in the above reaction scheme, after which the ester group was reduced to form an alcohol, which was then subjected to a Swerm oxidation (Synthesis, 1978, 297) conditions to convert into the intended S-aldehyde compound (C).

The chiral tin (II) Lewis acid could be obtained, for example, from tin (II) triflate and various chiral diamine, and a variety of such substances were proven to be useful in the synthesis of an aldol-type addition reaction product.

Example 2

Synthesis of β-aminoketone Compound (D)

A β-aminoketone compound (D) was prepared according to the following reaction scheme.

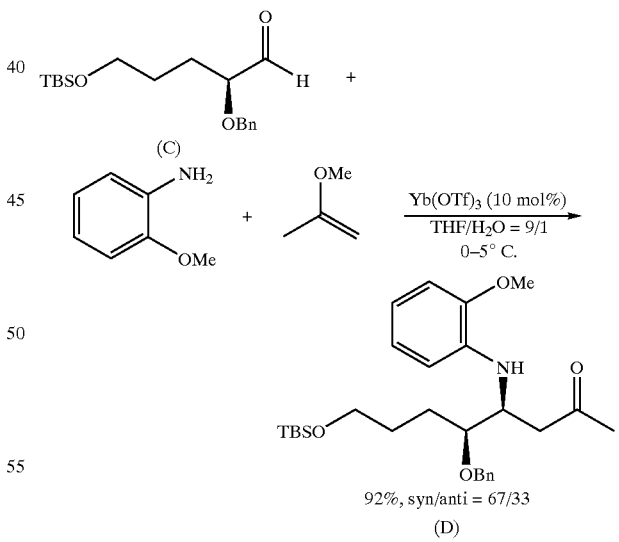

That is, the S-aldehyde compound (C) obtained in the above Example 1 was reacted with 2-methoxyaniline and 2-methoxypropene in the presence of 10 mol % of ytterbium triflate (Yb(OTf)$_3$) in an aqueous solvent consisting of a mixture of tetrahydrofuran (THF) and water (THF/H$_2$O=9/1) at a temperature of 0 to 5° C.

A β-aminoketone compound was obtained as the Mannich reaction product at a 92% yield (Syn/anti=67/33).

Example 3

Synthesis of Febrifugine (A)

Febrifugine (A) was prepared according to the reaction scheme shown below.

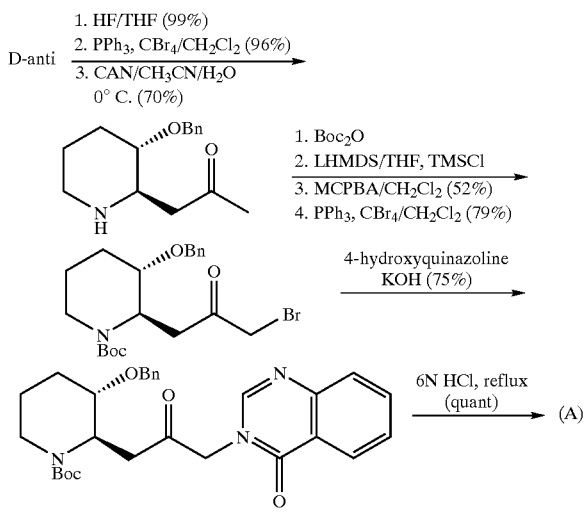

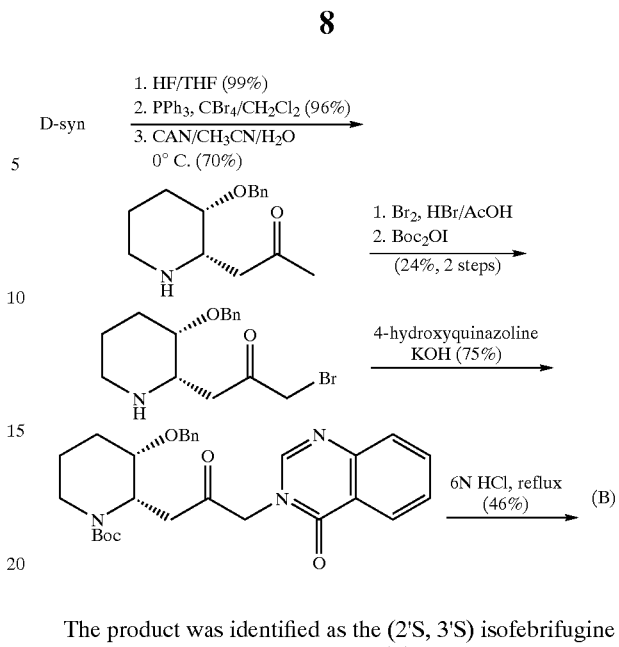

The product was identified as the (2'S, 3'S) isofebrifugine represented by the above Formula (B).

Example 5

Production of Febrifugine (A)

Using 2-methoxypropene having a p-methoxybenzyloxy group instead of 2-methoxypropene employed in Example 2, and also using a scandium trisdodecylsulfate (STDS) as a Lewis acid-surfactant-integrated catalyst instead of the triflate of ytterbium used as a rare earth metal in Example 2, a β-aminoketone compound was produced in water according to the reaction scheme shown below, and then converted to febrifugine (A) as in Example 3.

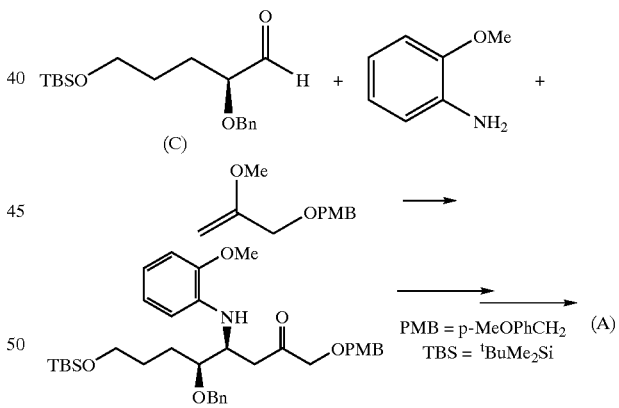

Febrifugine (A) was obtained almost quantitatively.

Example 6

The febrifugine and the isofebrifugine represented by Formulas (A) and (B) obtained by the methods of the present invention were examined for their activity against tropical malarial protozoan together with previously known compounds represented by the above Formulas ($A_0$) and ($B_0$).

Culture Assay of Tropical Fever Malarial Protozoan

In this experiment, *P. falciparum* FCR-3 strain (ATCC 30932) was employed as the tropical fever malarial protozoan. In order to verify the effect of the commercially The anti-diastereomer of the β-aminoketone compound obtained in Example 2 as the Mannich reaction product was treated with HF to eliminate the TBS protecting group and cyclized by bromination, after which the 2-methoxyphenyl group as an N-protecting group was eliminated using cerium ammonium nitrate (CAN). As a result, a pyperidine compound was obtained.

Then, the N atom of the pyperidine compound was protected as an N-Boc group and treated sequentially with lithium hexamethyl disilazide (LHMDS) followed by trimethylsilyl chloride (TMSCl).

The silylenol ether thus obtained was oxidized, then brominated, to obtain a pyperidine brominated acetone compound.

This substance was coupled with 4-hydroxyquinazoline using KOH (75%) and the resulting addition product was treated with 6N HCl to eliminate the protecting group.

As a result, a febrifugine (A) was obtained quantitatively.

After recrystallization from ethanol, the $^1$H and $^{13}$C NMR spectra and the melting point (MP) were measured.

The $^1$H NMR and $^{13}$C NMR spectra were identical to those reported previously, and the melting point was 138 to 140° C. which was within the range reported.

The optical rotation, however, was negative as reflected by $[\alpha]_D^{24}$ -28.0°(C=0.24, EtOH) which differed from the previously reported positive value $[\alpha]_D^{25}$ +28°(C=0.5, EtOH) (Koepfly, J. B.: Mead, J. F.; Brockman, Jr., J. A. J. Am. Chem. Soc., 1949, 71, 1048).

Based on the findings described above, the product was identified as a (2'R, 3'R) febrifugine represented by the above Formula (A).

Example 4

Production of Isofebrifugine (B)

Isofebrifugine (B) was prepared by procedures similar to those of Example 3 according to the reaction scheme shown below.

available anti-malarial agent chloroquin on resistant strains, a chloroquin resistant malarial protozoan of the *P. falciparum* K1 strain was employed. The medium used in this experiment was a filter-sterilized RPMI1640 medium which was adjusted to pH 7.4 and supplemented with 10% human serum. The malarial protozoan was cultured under 5% $O_2$, 4% $CO_2$ and 90% $NO_2$ at 36.5° C. The hematocrit level (% volume of erythrocyte in erythrocyte suspension) was adjusted to 5% for use. The initial infection rate with the tropical fever malarial protozoan at the beginning of the cultivation was 0.1%. The cultivation was performed using a 24-well cultivation plate, replacing the culture medium everyday, and subcultured at an infection rate of 4%. The infection rate was obtained by making a thin layer smear preparation, which was subjected to Giemsa staining or Diff-Qick staining, and observed microscopically (immersed in oil, magnified to ×1000) after which the malarial protozoan infection rate was determined using the following equation.

Malarial protozoan infection rate=[(number of infected erythrocyte)/(total number of erythrocyte)]×100

Test 1

Screening of Malarial Protozoan Growth Inhibition

The cultured malarial protozoan-infected erythrocyte was collected by centrifugation, and washed with a serum-supplemented medium, after which a non-infected erythrocyte was added to adjust the initial infection rate to 0.3%. At this time, the hematocrit rate was 3%. The sample used in the test was obtained by dissolving in sterilized water, dimethylformamide (DMF), or dimethylsulfoxide (DMSO) to create samples of desired concentration.

5 to 10 µl of the sample were added to a 24-well cultivation plate. The samples were tested in duplicates or triplicates. As a control, 10 µl/well of sterilized water, DMF or DMSO was employed.

Subsequently, to the above medium, 990 to 995 µl of the tropical fever malarial protozoan culture medium previously prepared were added by gentle pipetting to create a uniform suspension. The culture plate was incubated for 72 hours in a $CO_2$—$O_2$—$N_2$ (5%, 5%, 90%) incubator, after which thin layer smear preparations of each well was made, stained, and observed microscopically, to determine the infection rate together with the infection rate for the control.

From the malarial protozoan infection rate obtained by the method described above, the reproductive rate was calculated, whereby obtaining the 50% growth inhibition concentration ($EC_{50}$) for malarial protozoan. The results are shown in Table 1.

Reproductive rate={([b]-[a])/([c]-[a])}×100 a: initial infection rate
b: infection rate with sample added
c: infection rate without sample (Control)

Test 2

Mouse FM3A Cell Growth Inhibition Test

An F28-7 strain, a wild cell strain derived from mouse breast cancer FM3A cells was employed. A medium was prepared by supplementing an ES medium with 2% inactivated fetal calf serum, and incubated at 37° C. under 5% $CO_2$. Under these conditions, the doubling time of the FM3A cell was about 12 hours.

Following preincubation, the cells in logarithmic growth phase were diluted with the medium to $5 \times 10^4$ cells/ml. The sample used was one prepared for the anti-malarial activity test of the malaria protozoan. 5 to 10 µl of the samples were added to a 24-well cultivation plate (final concentration after addition of medium was $1 \times 10^{-4}$ to $1 \times 10^{-6}$). The compounds were tested in duplicates or triplicates, and wells containing 10 µl of sterilized water, DMF or DMSO were also prepared as a control. Subsequently, 990 to 995 µl of the cultured cell suspension previously prepared were added by gentle pipetting, and uniformly suspended in the medium. After incubating for 48 hours, the number of cells in each well was counted using SELF CONTROLLER (CC-108, Toa Medical Electrics) and the reproductive rate was calculated by using the following equation.

Reproductive rate (%)={([C]-[A])/([B]-[A])}×100

A: initial number of cells
B: number of control cell after 48 hours
C: number of cells after 48 hours from sample addition The cell growth inhibition activity was calculated from the number of cells in the well containing the sample and the number of cells in the control. From the results thus obtained, the cytotoxicity of each sample was evaluated and represented as the cell growth inhibition concentration ($EC_{50}$). The $EC_{50}$ value is the concentration (expressed as molar concentration) of a sample necessary to inhibit the reproductive rate of the control by 50%, wherein the reproductive rate or the rate of malarial protozoan infection for the control in which samples are not added to the medium of malarial protozoan or FM3A cell, is regarded as 100%. The results are shown in Table 1.

The anti-malarial effect of the sample was evaluated based on the ratio of the $EC_{50}$ of the sample for malarial protozoa to the $EC_{50}$ of the sample for FM3A cell (chemotherapeutic coefficient, see the equation shown below), from which the drug efficacy was determined.

The results are shown in Table 1.

Chemotherapeutic coefficient=[$EC_{50}$ of the sample for mouse FM3A cell]/[$EC_{50}$ of the sample for tropical fever malarial protozoan]

TABLE 1

| Sample | *P. falciparum* $EC_{50}$ (M) | FM3A $EC_{50}$ (M) | Ratio of Selective Toxicity for Malarial Protozoan <chemotherapeutic coefficient> |
| --- | --- | --- | --- |
| A | $3.0 \times 10^{10}$ | $8.0 \times 10^{-7}$ | 2667 |
| $A_0$ | $1.9 \times 10^{-7}$ | $2.0 \times 10^{-5}$ | 105 |
| B | $7.6 \times 10^{-11}$ | $2.2 \times 10^{-7}$ | 2895 |
| $B_0$ | $2.0 \times 10^{-7}$ | $2.2 \times 10^{-5}$ | 110 |

As can be seen from Table 1, febrifugine (A) and isofebrifugine (B) of the present invention showed selective malarial protozoan growth inhibiting activity, while formerly known substances only showed low activity.

INDUSTRIAL APPLICABILITY

As described in detail above, the present invention provides a febrifugine and an isofebrifugine as novel compounds having extremely strong activities against tropical malarial protozoan. The present invention also provides a novel production method which enables efficient large scale synthesis to establish a total synthesis route.

What is claimed is:

1. A method for producing febrifugine which comprises subjecting an S-aldehyde compound represented by Formula (C):

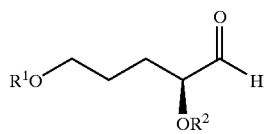

(wherein $R^1$ represents a silyl group and $R^2$ represents a cyclic hydrocarbon group) to a Mannich reaction with a 2-alkoxyaniline compound and a 2-alkoxypropane compound in the presence of an aqueous Lewis acid of a rare earth metal, in an aqueous solvent, to form a diastereomeric mixture of a β-aminoketone compound represented by Formula (D):

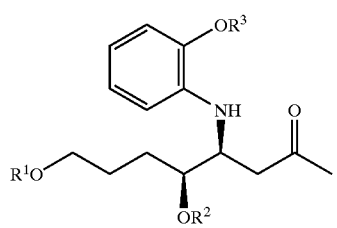

(wherein $R^1$ and $R^2$ are as defined above, and $R^3$ represents an alkyl group which forms an alkoxy group of the 2-alkoxyaniline), after which the anti-diastereomer is cyclized to form a piperidine compound, and reacted with a quinazoline compound to obtain a febrifugine represented by Formula (A):

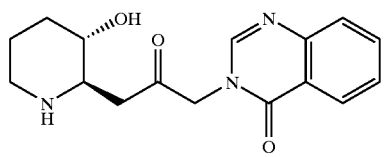

2. A method for producing febrifugine according to claim 1, wherein a silyloxypropanal represented by Formula (E):

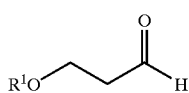

(wherein $R^1$ represents a silyl group) and an ethene compound represented by Formula (F):

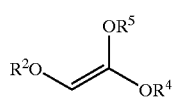

(wherein $R^2$ represents a benzyl group, $R^4$ represents an aromatic hydrocarbon group and $R^5$ represents a silyl group) are subjected to an asymmetric aldol condensation in the presence of a chiral tin (II) Lewis acid catalyst, to form an addition reaction product represented by Formula (G):

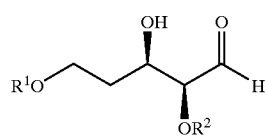

(wherein $R^1$, $R^2$ and $R^4$ are as defined above), dehydroxylated, and reduced to form the aldehyde compound of Formula (C), which is then subjected to the Mannich reaction.

3. A method for producing isofebrifugine which comprises subjecting an S-aldehyde compound represented by Formula (C):

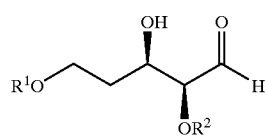

(wherein $R^1$ represents a silyl group and $R^2$ represents a cyclic hydrocarbon group) to a Mannich reaction with a 2-alkoxyaniline compound and a 2-alkoxypropane compound in the presence of an aqueous Lewis acid of a rare earth metal, in an aqueous solvent, to form a diastereomeric mixture of a β-aminoketone compound represented by Formula (D):

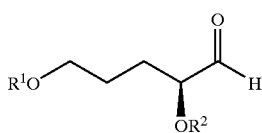

(wherein $R^1$ and $R^2$ are as defined above, and $R^3$ represents an alkyl group which forms an alkoxy group of the 2-alkoxyaniline), after which the syn-diastereomer is cyclized to form a piperidine compound, and reacted with a quinazoline compound to obtain a febrifugine represented by Formula (B):

4. A method for producing isofebrifugine according to claim 3, wherein a silyloxypropanal represented by Formula (E):

(wherein $R^1$ represents a silyl group) and an ethene compound represented by Formula (F):

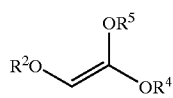
(F)

(wherein $R^2$ represents a cyclic hydrocarbon group, $R^4$ represents an aromatic hydrocarbon group and $R^5$ represents a silyl group) are subjected to an asymmetric aldol condensation in the presence of a chiral tin (II) Lewis acid catalyst, to form an addition reaction product represented by formula (G):

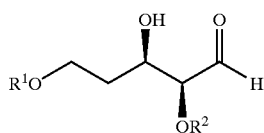
(G)

(wherein $R^1$, $R^2$ and $R^4$ are as defined above), dehydroxylated, and reduced to form the aldehyde compound of Formula (C), which is then subjected to the Mannich reaction.

5. A method for producing febrifugine, which comprises reacting an aldehyde compound represented by Formula (C)

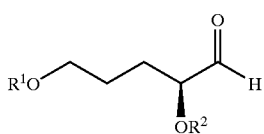
(C)

(wherein $R^1$ represents a silyl group and $R^2$ represents a cyclic hydrocarbon group) with a 2-alkoxydianiline compound and a 2-alkoxypropene compound by a Mannich reaction in water, in the presence of a Lewis acid-surfactant-integrated catalyst to form a β-aciketone compound.

6. A method for producing isofebrifugine, which comprises reacting an aldehyde compound represented by Formula (C)

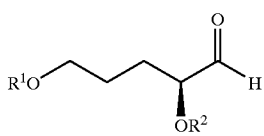
(C)

(wherein $R^1$ represents a silyl group and $R^2$ represents a cyclic hydrocarbon group) with a 2-alkoxydianiline compound and a 2-alkoxypropene compound by a Mannich reaction in water, in the presence of a Lewis acid-surfactant-integrated catalyst to form a β-aciketone compound.

* * * * *